US011655437B2

(12) United States Patent
Becker et al.

(10) Patent No.: US 11,655,437 B2
(45) Date of Patent: May 23, 2023

(54) DELIVERY SYSTEMS FOR PEROXIDE COMPOUNDS AND THEIR APPLICATIONS

(71) Applicant: Arkema Inc., King of Prussia, PA (US)

(72) Inventors: Christian Guy Becker, King of Prussia, PA (US); Pan Pan, King of Prussia, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/651,403

(22) PCT Filed: Sep. 14, 2018

(86) PCT No.: PCT/US2018/051017
§ 371 (c)(1),
(2) Date: Mar. 27, 2020

(87) PCT Pub. No.: WO2019/067232
PCT Pub. Date: Apr. 4, 2019

(65) Prior Publication Data
US 2020/0299621 A1     Sep. 24, 2020

Related U.S. Application Data

(60) Provisional application No. 62/564,311, filed on Sep. 28, 2017.

(51) Int. Cl.
| | | |
|---|---|---|
| *C11D 11/00* | (2006.01) | |
| *C11D 3/39* | (2006.01) | |
| *C11D 7/10* | (2006.01) | |
| *C11D 7/12* | (2006.01) | |
| *C11D 7/20* | (2006.01) | |
| *C11D 7/26* | (2006.01) | |
| *C11D 17/00* | (2006.01) | |
| *A61K 8/22* | (2006.01) | |
| *A61K 8/25* | (2006.01) | |
| *A61Q 11/00* | (2006.01) | |
| *A61Q 11/02* | (2006.01) | |
| *A61Q 17/00* | (2006.01) | |
| *A61Q 5/08* | (2006.01) | |
| *C11D 7/08* | (2006.01) | |

(52) U.S. Cl.
CPC ............ *C11D 11/0088* (2013.01); *A61K 8/22* (2013.01); *A61K 8/25* (2013.01); *A61Q 5/08* (2013.01); *A61Q 11/00* (2013.01); *A61Q 11/02* (2013.01); *A61Q 17/005* (2013.01); *C11D 3/3947* (2013.01); *C11D 7/08* (2013.01); *C11D 7/10* (2013.01); *C11D 7/12* (2013.01); *C11D 7/20* (2013.01); *C11D 7/26* (2013.01); *C11D 11/0017* (2013.01); *C11D 17/0034* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 4,008,170 A | | 2/1977 | Allan |
| 4,247,537 A | * | 1/1981 | Lunn ..................... A61K 8/22 8/111 |
| 4,839,157 A | * | 6/1989 | Mei-King Ng ........ A61K 8/042 424/53 |
| 5,008,093 A | | 4/1991 | Merianos |
| 6,413,548 B1 | | 7/2002 | Hamer et al. |
| 2006/0229210 A1 | | 10/2006 | Neugebauer et al. |
| 2006/0278847 A1 | | 12/2006 | Waizer et al. |
| 2007/0055009 A1 | | 3/2007 | Hasenzahl et al. |
| 2009/0252815 A1 | | 10/2009 | Walzer et al. |
| 2014/0120178 A1 | | 5/2014 | Hines et al. |
| 2014/0227333 A1 | | 8/2014 | Smith et al. |

FOREIGN PATENT DOCUMENTS

| | | | |
|---|---|---|---|
| DE | 2013763 | A1 | 10/1971 |
| EP | 1900799 | A2 | 3/2007 |
| GB | 906970 | | 9/1962 |
| KR | 20170010239 | | 1/2017 |
| WO | 2002018549 | A1 | 2/2006 |
| WO | WO-2006018549 A1 * | | 2/2006 ............ C11D 3/124 |

OTHER PUBLICATIONS

Aerosil product information sheet obtained from the websties: https://products-re.evonik.com/www2/uploads/productfinder/AEROSIL-R-202-EN.pdf (Year: 2019).*
Aerosil product information sheets obtained from the websties: https://products-re.evonik.com/www2/uploads/productfinder/AEROSIL-R-805-EN.pdf (Year: 2019).*
Aerosil™-Fumed Silica Technical Overview obtained from the website: https://www.l-i.co.uk/contentfiles/270.pdf (Year: unknown).*
Machine-assisted English translation for WO 2006/018549A1 (Year: 2006).*

(Continued)

*Primary Examiner* — Sin J Lee
(74) *Attorney, Agent, or Firm* — Lynn B. Morreale (57) ABSTRACT

A peroxide delivery system is produced. The peroxide delivery system includes a dry powder that releases the peroxide quickly and completely when needed. The peroxide delivery system may be produced by combining a liquid peroxide or peroxide solution with an inorganic solid support that is inert to the peroxide and is capable of adsorbing large amounts of the liquid peroxide or peroxide solution while remaining dry to the touch. Methods of combining the inorganic solid support with the liquid peroxide or peroxide solution are disclosed. The peroxide delivery system can be formulated in preparations of powders, liquids, foams, sprays, gels, ointments, creams, sticks, or pastes that can be utilized in a variety of applications such as cleaning, stain removal and antiseptic products, for example.

35 Claims, 3 Drawing Sheets

(56) References Cited

OTHER PUBLICATIONS

Adsorption of hydrogen peroxide on functionalized mesoporous silica surfaces; David Lewandowski et al; Stuct Chem (2014) 25: 1505-1512.
Chemical Engineering Research & Design—Dry water: From physico-chemical aspects to process-related parameters; Khashayar Saleh et al; 89 (2011) 537-544.
Powder Technology 189 (2009) 263-269; Influence of mixing characteristics for water encapsulation by self-assembling hydrophobic silica nanoparticles; Laurent Forny et al.
Current Opinion in Colloid & Interface Science 16 (2011) 266-271; Liquid Marbles: Properties and Applications; Edward Bormashenko.
Journal of Colloid & Interface Science 366 (2012) 16-22; Preparation of aqueous core/silica shell microcapsules; Keith Bean et al.
Science Direct—Colloids & Surfaces B: Biointerfaces 54 (2007) 165-172; Silica xerogei-hydrogen peroxide composites: Their morphology, stability & antimicrobial activity. Jacek Zegiinski et al.
Science Direct—Powder Technology 171 (2007) 15-24; Storing water in powder form by self-assembling hydrophobic silica nanoparticles; Laurent Forny et al.
Journal of Colloid & Interface Science 333 (2009) 419-421; Water rolling & floating upon water: Marbles supported by a water/marble interface; E. Bormashenko et al.
Science Direct—Colloids and Surfaces B: Biointerfaces 54 (2007) 165-172; Silica xerogel-hydrogen peroxide composites: Their morphology, stability and antimicrobial activity. Jacek Zegiinski et al.
Ecolab: "Oxonia Active", Oct. 15, 2014.
Evonik: "Aerosil R 812 S Hydrophobic fumed silica", Apr. 1, 2022.
Elsevier ScienceDirect—"Effect of the Drying Techniques on the Morphology of Silica Nanoparticles Synthesized Via Sol-Gel Process", Ceramics International 34 (2008) pp. 2059-2066.

\* cited by examiner

DELIVERY SYSTEMS FOR PEROXIDE COMPOUNDS AND THEIR APPLICATIONS

This present application is the national phase under 35 USC § 371 of prior PCT International Application Number PCT/US2018/051017 filed Sep. 14, 2018 which designated the United States of America and claimed priority to U.S. Provisional Patent Application Ser. No. 62/564,311 filed Sep. 28, 2017.

FIELD OF THE INVENTION

A delivery system for at least one peroxide compound is disclosed. The delivery system is prepared by combining solutions of at least one peroxide compound with a crystalline or amorphous solid material. The delivery system is dry to the touch and the peroxide compound is stable for long periods of time. Stabilizers for the peroxide compound can be added to the delivery system.

BACKGROUND OF THE INVENTION

Liquid peroxides and solutions of peroxide compounds are useful for many applications from industrial sources of oxidizers and free radicals to cosmetics and household sanitizers, but because they generally are liquid, unstable and reactive, convenient storage and delivery has long been a challenge.

A solid form of a peroxide compound that could take the form of a dry powder, pellet, tablet, bead, or brick, having long term stability, would have a broad range of applications: formulations for personal care, cosmetic, agriculture, and health care applications, to mention only a few.

Peroxides are notoriously reactive and thus resist attempts to be encapsulated chemically. Attempts to do so have generally been complicated, multistep processes that are extremely sensitive to reaction conditions and require expensive reagents and equipment, even on a laboratory scale. Few such products are available in commercial quantities.

The present disclosure provides a technology and a process for preparing a solid form of peroxide. A non-liquid peroxide in the form of solid, powder, granules, or blocks is often desired in applications such as toothpastes, anti-odor sticks, bleaching creams, or carpet cleaning because such formulations (and their rheological characteristics) are sensitive to liquid content. In other applications, peroxide cannot be handled or delivered in a liquid form, such as in air filters or in some surface treatments, and therefore must be delivered in a solid form.

Therefore, there is a long-felt need for a peroxide delivery system that can be produced with relatively cost-effective materials, using easily scaled-up, robust production methods. Further, a peroxide delivery system that has long term-stability, can be handled like a powder, can be easily mixed into a desired matrix or reaction media and yet is capable of delivering the peroxide compound using non-toxic materials that are safe for personal care products and additionally are not harmful to the environment has potential for large appeal.

SUMMARY OF THE INVENTION

A delivery system for at least one peroxide compound is disclosed. The delivery system uses an inorganic solid support that is inert to the peroxide compound and is capable of adsorbing a considerable quantity of liquid while remaining dry to the touch. The peroxide compound itself can be a liquid or is provided in a liquid solution that is capable of being adsorbed by the inorganic solid support. A stabilizer for the peroxide can be included in the peroxide delivery system.

The peroxide delivery system thus provided is in a solid form and has long-term stability. The peroxide is easily released merely by mixing the delivery system into the desired matrix or reaction media.

Various non-limiting aspects of the invention may be summarized as follows:

Aspect 1: A delivery system for at least one peroxide compound comprising:
 a) an inorganic solid support, wherein the inorganic solid support is inert to the at least one peroxide compound and is capable of adsorbing a liquid while remaining dry to the touch; and
 b) the at least one peroxide compound, wherein the at least one peroxide compound is a liquid peroxide or is in a liquid solution and the liquid peroxide or the liquid solution is capable of being adsorbed by the inorganic solid support;
 whereby the at least one liquid peroxide or the at least one peroxide compound in liquid solution is combined with the inorganic solid support, thereby forming the delivery system for the at least one peroxide compound.

Aspect 2: The delivery system for the at least one peroxide compound according to aspect 1, wherein the liquid peroxide or the liquid solution further comprises at least one stabilizer for the at least one peroxide compound.

Aspect 3: The delivery system for the at least one peroxide compound according to aspect 1 or aspect 2, wherein the inorganic solid support has a pH less than 6.

Aspect 4: The delivery system for the at least one peroxide compound according to any of aspects 1-3 wherein the inorganic solid support comprises less than 50 ppm of any individual contaminant selected from the group consisting of Al, Ca, Fe, K, Mg, Ti, and Zr.

Aspect 5: The delivery system for the at least one peroxide compound according to any of aspects 1-4, wherein the inorganic solid support comprises fumed silica.

Aspect 6: The delivery system for the at least one peroxide compound according to any of aspects 1-5, wherein the at least one peroxide compound comprises a solution of hydrogen peroxide in water.

Aspect 7: The delivery system for the at least one peroxide compound according to aspect 5, wherein the fumed silica has a pH less than 6.

Aspect 8: The delivery system for the at least one peroxide compound according to aspect 5 or aspect 7, wherein the fumed silica comprises hydrophilic fumed silica and the at least one peroxide compound is in a liquid solution comprising a solution of hydrogen peroxide in water.

Aspect 9: The delivery system for the at least one peroxide compound according to aspect 6 or aspect 8, wherein the solution of hydrogen peroxide in water further comprises at least one stabilizer for hydrogen peroxide.

Aspect 10: The delivery system for the at least one peroxide compound according to any of aspects 5, 7 or 8, wherein the fumed silica comprises less than 50 ppm of any individual contaminant selected from the group consisting of Al, As, Ba, Ca, Cd, Co, Cr, Cu, Fe, K, Mg, Mn, Mo, Na, Ni, P, Pb, Sb, Si, Sn, Sr, Ti, V, W, Zn, and Zr.

Aspect 11: The delivery system for the at least one peroxide compound according to any of aspects 5 or 7-10 wherein the fumed silica comprises less than 50 ppm of any individual contaminant selected from the group consisting of Al, Ca, Fe, K, Mg, Ti, and Zr.

Aspect 12: The delivery system for the at least one peroxide compound according to any of aspects 5 or 7-11, wherein the fumed silica comprises less than 10 ppm of any individual contaminant selected from the group consisting of Al, Ca, Fe, K, Mg, Ti, and Zr.

Aspect 13: The delivery system for the at least one peroxide compound according to any of aspects 5 or 7-12 wherein the fumed silica comprises hydrophilic fumed silica and the at least one peroxide compound is in a liquid solution comprising a solution of hydrogen peroxide in water.

Aspect 14: The delivery system for the peroxide compound according to any of aspects 6, 8 or 9, wherein the solution of hydrogen peroxide in water further comprises a stabilizer for the hydrogen peroxide.

Aspect 15: The delivery system for the at least one peroxide compound according to aspect any of aspects 6 or 8-10, wherein the solution of hydrogen peroxide in water comprises at least 0.001% by weight of the stabilizer for hydrogen peroxide.

Aspect 16: The delivery system for the at least one peroxide compound according to any of aspects 1-15 wherein the delivery system has a total delivery system weight and the at least one liquid peroxide or the at least one peroxide compound in the solution of liquid has a liquid peroxide weight or a peroxide liquid solution weight and wherein the liquid peroxide weight or the peroxide liquid solution weight comprises at least 70% of the total delivery system weight.

Aspect 17: The delivery system for the at least one peroxide compound according to any of aspects 1-16 wherein the liquid peroxide weight or the peroxide liquid solution weight comprises at least 50% of the total delivery system weight.

Aspect 18: The delivery system for the at least one peroxide compound according to any one of aspects 6, 8, or 9, wherein the solution of hydrogen peroxide in water comprises at least 50% by weight of hydrogen peroxide.

Aspect 19: The delivery system for the at least one peroxide compound according to any of aspects 6, 8, 9 or 18, wherein the solution of hydrogen peroxide in water comprises at least 70% hydrogen peroxide.

Aspect 20: The delivery system for the at least one peroxide compound according to any of aspects 13-15 wherein the solution of hydrogen peroxide in water comprises at least 50% hydrogen peroxide.

Aspect 21: The delivery system for the at least one peroxide compound according to any of aspects 13-15 or 20 wherein the solution of hydrogen peroxide in water comprises at least 70% hydrogen peroxide.

Aspect 22: The delivery system for the at least one peroxide compound according to any of aspects 1-21, wherein the at least one peroxide compound is selected from the group consisting of hydrogen peroxide, peracetic acid, perborates, percarbonates, organic peroxides, persulfate salts, peroxyacids, and mixtures thereof.

Aspect 23: The delivery system for the at least one peroxide compound according to any of aspects 2, 9, 14 or 15, wherein the stabilizer is selected from the group consisting of stannates, polyols, diols, carboxylates, phosphates, pyrophosphates, ethylenediaminetetraacetic acid (EDTA) and salts thereof, amine-substituted organophosphonic acids and their salts, adipic acid and salts thereof, phosphoric acid and salts thereof, succinic acid and salts thereof, butylated hydroxytoluene (BHT), butylated hydroxyanisole (BHA), phenols, and mixtures thereof.

Aspect 24: A delivery system for at least one peroxide compound comprising:
  a) fumed silica, wherein the fumed silica is inert to the at least one peroxide compound, is capable of adsorbing up to 70% of a liquid by weight of the delivery system while remaining dry to the touch, has a pH less than 6, and contains less than 50 ppm of any individual contaminant selected from the group consisting of Al, Ca, Fe, K, Mg, Ti, and Zr; and
  b) the at least one peroxide compound wherein the at least one peroxide compound is a liquid peroxide or is a solution of the at least one peroxide compound in liquid, wherein the liquid peroxide or the solution of at least one peroxide in liquid is capable of being adsorbed by the fumed silica and wherein the liquid peroxide or the solution of the at least one peroxide in liquid contains at least 0.001% of a stabilizer for the peroxide;
  whereby up to 70% of the liquid peroxide or the solution of the at least one peroxide compound in liquid by weight of the delivery system is combined with the fumed silica, thereby forming the delivery system for the at least one peroxide compound.

Aspect 25: A delivery system for hydrogen peroxide comprising:
  a) hydrophilic fumed silica, wherein the hydrophilic fumed silica is inert to hydrogen peroxide, is capable of adsorbing up to 70% of liquid by weight of the delivery system while remaining dry to the touch, has a pH less than 6, and contains less than 50 ppm of any individual contaminant selected from the group consisting of Al, Ca, Fe, K, Mg, Ti, and Zr; and
  b) a solution of hydrogen peroxide in water, wherein the solution of hydrogen peroxide in water is capable of being adsorbed by the hydrophilic fumed silica and contains at least 0.001% of a stabilizer for the hydrogen peroxide;
  whereby up to 70% of the solution of hydrogen peroxide in water by weight of the delivery system is combined with the hydrophilic fumed silica, thereby forming the delivery system for hydrogen peroxide.

Aspect 26: The delivery system for the at least one peroxide compound according to any of aspects 1-25, wherein the at least one peroxide compound has an initial active oxygen content and wherein the at least one peroxide compound retains at least 60% of the initial active oxygen content after storage for 1 week at 50° C.

Aspect 27: The delivery system for the at least one peroxide compound according to any of aspects 1-25, wherein the at least one peroxide compound has an initial active oxygen content and wherein the at least one peroxide compound retains at least 80% of the initial active oxygen content after storage for 1 week at 50° C.

Aspect 28: The delivery system for the at least one peroxide compound according to any of aspects 1-25, wherein the at least one peroxide compound has an initial active oxygen content and wherein the at least one peroxide compound retains at least 90% of the initial active oxygen content after storage for 1 week at 50° C.

Aspect 29: A method of removing stains from a stained fabric wherein the method comprises the steps of:
  a. providing the peroxide delivery system according to any of aspects 1-28;
  b. applying the peroxide delivery system to the stained fabric;

c. allowing the peroxide delivery system to stand on the stained fabric for a period of time; and
d. rinsing the peroxide delivery system from the stained fabric.

Aspect 30: An oral care composition comprising the peroxide delivery system of any of aspects 1-28.

Aspect 31: A toothpaste or tooth cleaning composition comprising the peroxide delivery system of any of aspects 1-28.

Aspect 32: A cleaning composition comprising the peroxide delivery system of any of aspects 1-28.

Aspect 33: A laundry cleaning composition comprising the peroxide delivery system of any of aspects 1-28.

Aspect 34: A floor cleaning composition comprising the peroxide delivery system of any of aspects 1-28.

Aspect 35: A cosmetic composition comprising the peroxide delivery system of any of aspects 1-28.

Aspect 36: A hair bleaching composition comprising the peroxide delivery system of any of aspects 1-28.

Aspect 37: A hair dye composition comprising the peroxide delivery system of any of aspects 1-28.

Aspect 38: An antiseptic composition comprising the peroxide delivery system of any of aspects 1-28.

DETAILED DESCRIPTION OF THE INVENTION

The solid supports useful in the invention are high purity, inorganic powders. The solid support (also called a carrier) for the peroxide compound is required to be inert to peroxide. As used herein, inert to peroxide means that the solid support does not react with the peroxide compound to be included in the delivery and further does not catalyze degradation (loss of active oxygen as measured by measured by titration using a Metrohm Autotitrator) of the peroxide compound in the delivery system. "Inert to peroxide" as used herein means that less than 10% of the initial active oxygen of the peroxide compound is lost upon storage of the delivery system in a sealed opaque container at 25° C. for 1 week.

As will be detailed below, extensive tests of both the long term stability for an exemplary peroxide compound in various carriers were conducted, as well as detailed analyses of the inorganic carriers to determine suitable ranges of impurities and other physical properties required of carriers for the peroxide delivery system.

The invention will be illustrated with a series of Examples. However, before providing detailed results, what follows is a summary of properties of the reagents that are used in the Examples.

Reagents:
Peroxide Compound:

Hydrogen peroxide was selected as the example peroxide compound to illustrate the invention. Five aqueous hydrogen peroxide solutions, having varying levels of peroxide and stabilizers, were used. They are shown in Table 1:

TABLE 1

| Hydrogen Peroxide Solutions | | |
| --- | --- | --- |
| Product (Arkema) | $H_2O_2$ level, percent w/w | Stabilizer level |
| Peroxal ® 50% CLG | 50 | high |
| Peroxal ® 50% EG | 50 | very low |
| Peroxal ® 70% CG | 70 | medium |
| Peroxal ® 50% CG | 50 | medium |
| Peroxal ® 50% CG-HP | 50 | very high |

Any type of stabilizer suitable for peroxides can be included in the peroxide delivery system. Products capable of stabilizing peroxides are known and available. Various amounts of peroxide stabilizers, peroxide stabilizers having different structures/compositions and combinations of stabilizers may be employed, depending on the final applications and markets in which the peroxide delivery system is employed. Non-limiting examples of suitable stabilizers are: stannates, polyols, diols, carboxylates, phosphates, pyrophosphates, ethylenediaminetetraacetic acid (EDTA) and salts thereof, amine-substituted organophosphonic acids or their salts, adipic acid and salts thereof, phosphoric acid and salts thereof, succinic acid and salts thereof, butylated hydroxytoluene (BHT), butylated hydroxyanisole (BHA), phenols, and combinations thereof. Any suitable level of stabilizer can be utilized, ranging from 1 ppm to 30% by weight of the peroxide solution or peroxide compound, if the peroxide itself is liquid. The relative amounts of stabilizers for the reagents used in the Examples is provided in Table 1

It should also be understood that while the Examples illustrate the invention with hydrogen peroxide in an aqueous solution as the peroxide compound, other peroxides and other solvents are also suitable for use in the peroxide delivery system. Non-limiting examples of such peroxides are: peroxyacids (e.g., peracetic acid), perborates, percarbonates, organic peroxides (including, for example, dialkyl peroxides, peroxyketals and organic hydroperoxides), persulfate salts, peresters, or mixtures of these chemicals. Any suitable solvent for the chosen peroxide compound may be used to produce the peroxide delivery system as disclosed herein. Water, organic solvents or aqueous organic solvents may be employed as the solvent, for example.

Solid Support: Precipitated Silica and Silica Gel

Precipitated silica is a form of silica produced by precipitation. The production of precipitated silica starts with the reaction of an alkaline silicate solution with a mineral acid. Sulfuric acid and sodium silicate solutions are added simultaneously with agitation to water and precipitation of the silica is carried out under alkaline conditions. The properties of the resulting precipitated silica can be controlled and manipulated depending on reaction conditions. The amount and type of agitation, duration of precipitation, the addition rate of reactants, their temperature and concentration, as well as the pH of the reaction mixture can all influence the properties of the precipitated silica thus produced. The formation of a gel stage is avoided by stirring at elevated temperatures (e.g., 85° C. to 95° C.). Carrying out the precipitation at a lower temperature (e.g., 20° C. to 30° C.) yields silica gel. The resulting white precipitate is filtered, washed and dried as part of the final stages of the manufacturing process.

Figure 1:
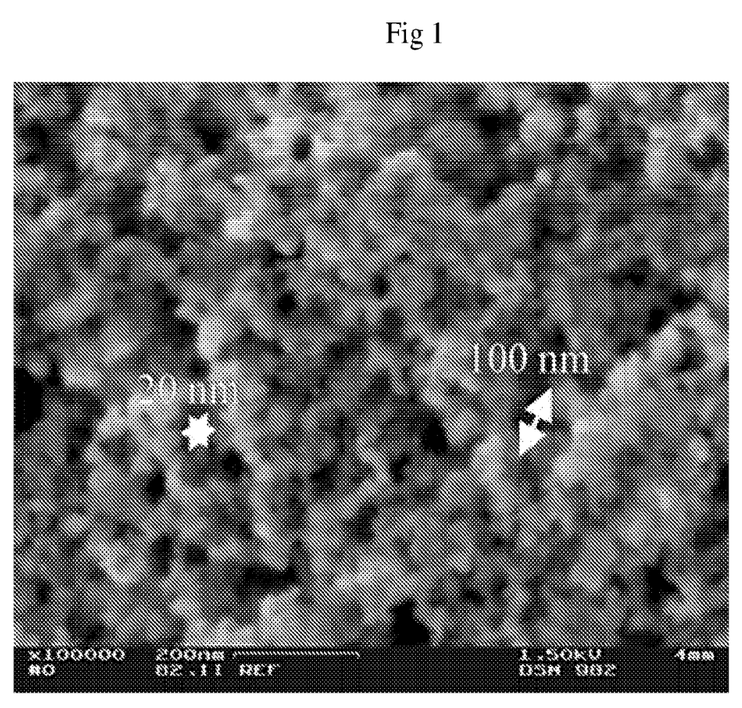
FIG. 1 shows a scanning electron microscope (SEM) micrograph of precipitated silica.

Precipitated silica is porous and therefore has the capacity to absorb liquid. An SEM micrograph of a precipitated silica is provided in FIG. 1.

Experiments were done with Sipernat® 500 LS and Sipernat® 22 LS precipitated silica (from Evonik) and Syloid® 244FP silica gel (from W. R. Grace). Syloid® silica products manufactured by W.R. Grace are synthetic amorphous silica gels of high purity.

Table 2 shows Sipernat® and Syloid® properties as provided by their manufacturers.

TABLE 2

Properties of precipitated silica and silica gel products used in Examples

| | Sipernat ® 22 LS (Evonik/ Degussa) | Sipernat ® 500 LS (Evonik/ Degussa) | Syloid ® 244FP (W. R. Grace) |
|---|---|---|---|
| Specific surface area ($m^2/g$) | 180 | 500 | 300 |
| Particle size $d_{50}$ (laser diffraction, μm) | 9.0 | 5.5 | 5.5 |
| Bulk density (g/l) | 70 | 70 | 60 |
| pH* | ≈6.2 | ≈6 | 7.0 |
| Pore volume (cc/g) | Not listed | Not listed | 1.5-1.6 |
| Grade | Industrial | Industrial | USP (food and pharmaceutical grade) |

*ISO 787/9

Solid Support: Hydrophilic Fumed (or Pyrogenic) Silica

Figure 2:
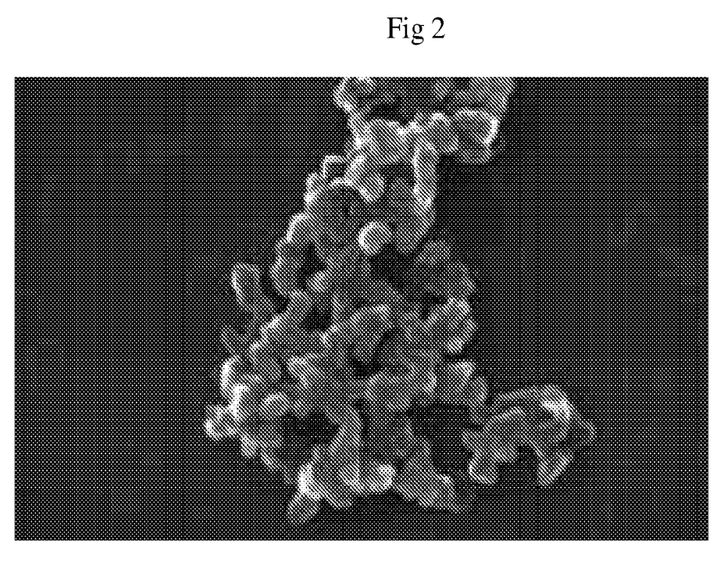
FIG. 2 shows an SEM micrograph of a single aggregate of fumed silica.

Fumed (also called pyrogenic) silica has a very different morphology from precipitated silica. Fumed silica products (e.g., Aerosil® from Evonik/Degussa and CAB-O-SIL® from Cabot) are characterized by an amorphous structure and a range of primary particle sizes. The primary particles do not exist in isolated form, but as aggregates and agglomerates. Fumed silica, also referred to as pyrogenic silica because it is produced in a flame, consists of microscopic droplets (the primary particles) of amorphous silica that are fused into branched, chainlike, three-dimensional secondary particles or aggregates which then agglomerate into tertiary particles. The individual microscopic droplets are essentially non-porous. The structure of these branched, chainlike, three-dimensional secondary particles or aggregates is clearly shown in the SEM in FIG. 2.

Fumed silica ($SiO_2$) is manufactured via a continuous flame hydrolysis of a substance such as silicon tetrachloride ($SiCl_4$). In the flame, hydrogen and oxygen (from the air) are reacted in the presence of $SiCl_4$. The formation of $SiO_2$ can be described by a combination of an oxyhydrogen reaction, in which water is formed. Hydrolysis of $SiCl_4$ with this water takes place such that $SiO_2$ is formed in the flame in fractions of a second. A mixture of hot gases and solids ($SiO_2$ particles) containing hydrochloric acid is produced as an aerosol. This aerosol first needs to be cooled down before being separated into solid and gases in the next process step. After separation, the solid still contains relatively large quantities of HCl, adsorbed onto the surface of the particles. A de-acidification step is performed to remove HCl from the hydrophilic product as the final step in producing untreated, hydrophilic fumed silica. The surface of untreated fumed silica, after the de-acidification step, is extremely hydrophilic, that is, the surface is easily wetted by water, due to the freely accessible silanol groups (Si—OH) on the surfaces of the particles. Without wishing to be bound by theory, it is speculated that because the individual primary particles of fumed silica are non-porous, that upon addition of a liquid, the liquid is not absorbed inside the fumed silica particles (as one might expect for precipitated silica which is porous) but remains on the surface of the branched, chainlike, three-dimensional secondary particles or aggregates which form larger agglomerates. Even though the agglomerates are formed of individual aggregates, one could appreciate that the intricate surface morphology of fumed silica aggregates and agglomerates should be sufficient to retain large amounts of liquid, if the liquid is able to wet the surface. Therefore, for aqueous or polar solutions of peroxide, hydrophilic fumed silica might be expected to adsorb a great deal of liquid.

Hydrophilic fumed silica can be subjected to a variety of post-treatment steps that can bind other moieties to its surface. Thus, hydrophilic fumed silica can be transformed into a fumed silica product that can be wetted by non-aqueous solutions of peroxide. Again, without wishing to be bound by theory, it is expected that such a treated fumed silica would similarly expected to be capable of adsorbing large amounts of a non-polar or non-aqueous solution of peroxide as long as the solution is capable of wetting the surface of such a surface-modified fumed silica. Non-limiting examples of non-aqueous peroxide solutions are: 2,2-Bis(t-butylperoxy)butane in a hydrocarbon solvent; 1,1-Bis (t-butylperoxy cyclohexane) in a hydrocarbon or aromatic hydrocarbon solvent; Cumene hydroperoxide in an aromatic solvent; p-Menthane hydroperoxide in a hydrocarbon solvent; isobutyryl peroxide in a hydrocarbon solvent; t-Butyl peroxy isopropyl monocarbonate in a hydrocarbon solution; α,α'-Bis(neodecanoyl peroxy)diisopropyl benzene in a hydrocarbon solvent; Cumyl peroxyneodecanoate in a hydrocarbon solvent; t-Hexyl peroxy pivalate in a hydrocarbon solvent; t-amyl peroxy pivalate in a hydrocarbon solvent; and t-Butyl peroxy 2-ethylhexanoate in a solution with plasticizer. Other non-limiting examples of suitable peroxides are those that are available as a neat liquid, either with or without stabilizer: t-amyl peroxy 2-ethylhexanoate; t-Butyl peroxy 3,5,5-trimethyl hexanoate; t-Butyl peroxybenzoate; t-Butyl peroxy 2-ethylhexanoate; t-Butyl peroxy 2-ethylhexyl monocarbonate; 2,5-Dimethyl-2,5-bis(t-butylperoxy) hexane; Di-t-Butyl peroxide; t-Butyl cumyl peroxide; 1,1,3,3-Tetramethylbutyl hydroperoxide; and n-Butyl 4,4-bis(t-butylperoxy) valerate.

Examples of typical particle geometries for fumed silica are listed in Table 3.

TABLE 3

Example of typical properties of fumed silica (Measured with TMZ device)

| | |
|---|---|
| Primary particle diameter | 12 nm |
| Mean primary particle diameter derived from specific surface area | 14 nm |
| Calculated specific TEM surface area | 220 $m^2/gm$ |

Aggregate-size measurement

| | |
|---|---|
| Mean projected aggregate surface area | 11675 $nm^2$ |
| Circumference | 1386 nm |
| Convex circumference | 521 nm |
| Minimum aggregate diameter | 117 nm |
| Maximum aggregate diameter | 198 nm |
| Void area | 28% |
| Degree of branching | 9.5 |
| Number of primary particles per aggregate | 436 |

Results of classification analysis

| Percent by class | | |
|---|---|---|
| | Spherical | 0.88 |
| | Ellipsoid | 13.2 |
| | Linear | 38.6 |
| | Branched | 47.4 |

TABLE 3-continued

Example of typical properties of fumed silica

| Percent by weight | Spherical | 0.03 |
|---|---|---|
| | Ellipsoid | 0.72 |
| | Linear | 8.6 |
| | Branched | 90.7 |

In order to confirm the suitability of fumed silica as the solid support for the peroxide delivery system, various hydrophilic fumed silica products were tested. These are listed with their properties as reported by the manufacturers in Table 4.

TABLE 4

Fumed silica products used in Examples

| Silica | Grade | Surface Area Range (m²/g) (ISO 9277) | pH (ISO 787/9) | Tamped Density (g/l) (ISO 787/11) |
|---|---|---|---|---|
| Aeroperl ® 300 Pharma (Evonik) | USP | 300 | 3.5-5.5 | 280 |
| CAB-O-SIL ® M-5P (Cabot) | USP | 200 | 3.6-4.5* | 30-150 |
| CAB-O-SIL ® M-5F (Cabot) | Food | 200 | 3.6-4.5* | 30-150 |
| CAB-O-SIL ® EH5F (Cabot) | Food | 385 | 3.6-4.5* | 30-150 |
| CAB-O-SIL ® M-5 (Cabot) | Industrial | 200 | 3.6-4.5* | 30-150 |
| Aerosil ® 300 Pharma (Evonik) | USP | 300 | 3.7-4.7 | 50 |
| Aerosil ® 200 Pharma (Evonik) | USP | 200 | 3.5-5.5 | 50 |
| Aerosil ® 300 (Evonik) | Industrial | 300 | 3.7-4.5 | 50 |
| Aerosil ® 200 (Evonik) | Industrial | 200 | 3.7-4.5 | 50 |

*in house testing by Cabot

Worldwide, there are many producers of fumed silica and other suitable materials are not limited to those studied here, nor to those made by other producers: e.g., Wacker Chemie AG: products sold under the brand name "HDK"; Orisil: products sold under the brand name "Orisil"; DC Chemical: products sold under the brand name "Konasil"; Tokuyama: products sold under the brand name "Reolosil"; or Xunyu: products sold under the brand name "Xysil".

Impurity Content of Precipitated Silica, Silica Gel and Fumed Silica Products

As used herein, the term impurity or contaminant refers to elements other than those that are expected to be in the solid support for the peroxide delivery system. In this example, the impurities or contaminants comprise elements other than Si, O and H that comprise fumed silica, silica gel or precipitated silica that have silanol groups on their surface. Surface-treated fumed or precipitated silica may comprise other moieties that are bonded to their surface and therefore could have slightly different elements that are considered to be impurities or contaminants. The impurity or contaminant contents of fumed silica, silica gel and precipitated silica products were measured by analyzing samples using inductively coupled plasma mass spectrometry or ICP-MS. Samples were analyzed on an Agilent 7700x ICP-MS after digestion in a microwave digester with nitric acid and sodium fluoride. Table 5 below shows the elements which leached out of the sample matrices during the digestion procedure.

It is apparent from Table 5 that impurity or contaminant contents are different in the various samples and play a role in the degradation of hydrogen peroxide (Table 6). The following elements: Al, Ca, Fe, K, Mg, Ti and Zr are present at a higher level in Sipernat® and Syloid® samples than in the other silica samples. These elements are either low in concentration or non-detected in the Aerosil® and CAB-O-SIL® samples.

TABLE 5

ICP-MS Results for various silica products

| Element (ppm) | Sipernat ® 500LS (Evonik) | Sipernat ® 22LS (Evonik) | Syloid ® 244FP (WRGrace) | CAB-O-SIL ® M-5F (Cabot) | CAB-O-SIL ® M-5 (Cabot) | Aerosil ® 300 Pharma (Evonik\Degussa) | Aerosil ® 300 (Evonik/Degussa) | Aeroperl ® 300 Pharma (Evonik/Degussa) |
|---|---|---|---|---|---|---|---|---|
| Al | 340 | 221 | 70 | N.D. | <0.86 | N.D. | 1.0 | 0.31 |
| As | N.D. | N.D. | N.D. | N.D. | N.D. | N.D. | N.D | N.D. |
| Ba | 1.3 | 1.2 | 2.5 | N.D. | N.D. | N.D. | N.D. | <0.01 |
| Ca | 90 | 63 | 144 | 1.2 | <0.39 | 0.55 | N.D. | 2.9 |
| Cd | <0.01 | <0.01 | <0.01 | N.D. | N.D. | N.D. | N.D. | N.D. |
| Co | 0.03 | 0.03 | <0.01 | N.D. | N.D. | N.D. | N.D. | 0.02 |
| Cr | 0.95 | N.D. | 0.45 | N.D. | N.D. | N.D. | N.D. | N.D. |
| Cu | 0.23 | 0.11 | 0.03 | <0.08 | <0.11 | 0.04 | <0.01 | N.D. |
| Fe | 157 | 109 | 17 | N.D. | N.D. | N.D. | N.D. | N.D. |
| K | 90 | 57 | 51 | 0.27 | <2 | <0.50 | <0.71 | 0.75 |
| Mg | 208 | 53 | 152 | 0.46 | <0.07 | 0.07 | <0.07 | 0.29 |
| Mn | 0.42 | 0.29 | 0.06 | N.D. | N.D. | N.D. | <0.08 | <0.01 |
| Mo | N.D. | N.D. | N.D. | N.D. | N.D. | N.D. | N.D. | <0.05 |
| Na | N.A. | N.A. | N.A. | N.A. | N.A. | N.A. | N.A. | N.A. |
| Ni | <0.02 | N.D. | 0.32 | 0.22 | N.D. | N.D. | 0.15 | 0.15 |
| P | N.D. | N.D. | N.D. | N.D. | N.A. | N.D. | N.A. | 1.3 |
| Pb | 0.89 | 0.28 | 0.08 | 0.03 | <0.01 | N.D. | N.D. | <0.01 |
| Sb | N.D. | N.D. | 0.01 | N.D. | N.D. | N.D. | N.D. | N.D. |
| Si | N.A. | N.A. | N.A. | N.A. | N.A. | N.A. | N.A. | N.A. |

TABLE 5-continued

ICP-MS Results for various silica products

| Element (ppm) | Sipernat® 500LS (Evonik) | Sipernat® 22LS (Evonik) | Syloid® 244FP (WRGrace) | CAB-O-SIL® M-5F (Cabot) | CAB-O-SIL® M-5 (Cabot) | Aerosil® 300 Pharma (Evonik\Degussa) | Aerosil® 300 (Evonik/Degussa) | Aeroperl® 300 Pharma (Evonik/Degussa) |
|---|---|---|---|---|---|---|---|---|
| Sn | N.D. | N.D. | N.D. | N.D. | <0.1 | N.D. | <1 | N.D. |
| Sr | 2 | 0.68 | 2 | N.D. | N.D. | N.D. | N.D. | N.D. |
| Ti | 72 | 57 | 73 | N.D. | N.D. | 0.12 | N.D. | 0.22 |
| V | .26 | 0.23 | 0.06 | N.D. | N.D. | <0.05 | N.D. | N.D. |
| W | N.D. | N.D. | 0.29 | N.D. | N.D. | N.D. | N.D. | N.D. |
| Zn | <0.10 | 0.51 | 0.69 | <0.01 | N.D. | N.D. | N.D. | 1.4 |
| Zr | 30 | 31 | 54 | N.D. | N.D. | 0.28 | N.D | 0.09 |

The invention will be illustrated with a series of Examples as follows:

EXAMPLES

Example 1: Preparation of Peroxide Delivery Systems

Process: The aqueous hydrogen peroxide solution was added slowly and continuously to the silica in order to distribute the solutions as uniformly as possible onto the silica carrier. The silica products, both precipitated and fumed, are in the form of very fluffy powders, which have the capacity to adsorb a great deal of liquid. Adding the liquid in a drop-wise manner or as a spray was the most effective method of adding the liquid to the silica powders. It is anticipated that the production technique on a large scale could encompass either batch-wise mixing, or continuous or semi-batch processes.

Mixing under high shear was not necessary. The powders easily adsorbed the liquid. The powder could form a few agglomerates which easily re-dispersed when the mixture was stirred thoroughly to homogenize it. If needed, the peroxide delivery system product could be pushed through a sieve, e.g., 1.4 mm (14 mesh) or any size smaller or larger as needed to break lumps, if they form. The resulting peroxide delivery system was a dry to the touch, completely friable and pulverulent powder. There is no need for solvent removal or any additional steps to this process.

Most of the silica products tested adsorbed more than their own weight of liquid. With a few exceptions (noted below), the silica powders were able to easily adsorb about 2⅓ times their weight of liquid, i.e. about 70% of the total weight of the peroxide delivery system (liquid plus silica) is the liquid portion.

As an example, the following ratios (weight silica:weight liquid) were used:

30% silica → 10.0 g
70% liquid → 23.3 g
(peroxide + solvent)
Total weight 33.3 g After mixing as described above, the resulting solid appeared as a dry, white powder. The mixtures were completely dry to the touch and the liquid did not seep out or otherwise cause the final powders to feel damp or wet even after long periods of storage. It was noted that the peroxide solutions would evaporate from the solid to some extent if the powders were left in unclosed containers for a period of time.

The peroxide delivery system made with Syloid® 244FP felt wet if it contained more than 56% liquid by total weight. Similarly, the peroxide delivery system made with Aeroperl® 300 Pharma felt wet if it contained more than 50% liquid by total weight.

Initial experiments were performed with hydrogen peroxide at 10% concentration (diluted from Peroxal® 50% CLG grade) in order to assess any potential safety issues. Once the procedure was safely established, peroxide delivery systems were produced using hydrogen peroxide at 50% concentration in water and also using a 70% solution of hydrogen peroxide in water.

Clearly, the hydrogen peroxide level in the final peroxide delivery system depends on the concentration of the hydrogen peroxide in the solution that is combined with the silica. Therefore, in the following tables, percent of $H_2O_2$ loading by weight refers to the weight percent of peroxide in the peroxide delivery system, not the total loading of the liquid solution, which contains both solvent and $H_2O_2$, in the delivery system. Thus:

weight percent $H_2O_2$ loading=[weight of $H_2O_2$/(weight of silica+weight of solvent+weight of $H_2O_2$)]100

A 10% solution of hydrogen peroxide provides a hydrogen peroxide loading in the delivery system of 7%, when the delivery system contains 70% by weight of solution.

A 50% solution of hydrogen peroxide provides a hydrogen peroxide loading in the delivery system of 35%, when the delivery system contains 70% by weight of solution.

A 70% solution of hydrogen peroxide provides a hydrogen peroxide loading in the delivery system of 49%, when the delivery system contains 70% by weight of solution.

Example 2: Stability of Hydrogen Peroxide in the Peroxide Delivery System

The silica products described above were combined with the various peroxide solutions according to the process described in Example 1 to form peroxide delivery systems that have varying peroxide loading levels, stabilization levels and types of silica. The initial active oxygen content, and active oxygen content after aging of each delivery system was measured by titration using a Metrohm Autotitrator. The titration data is accurate to within ±1 to 2%.

The peroxide delivery systems thus formed were stored in plastic bottles and held at 50° C. The active oxygen content was measured after 1 week, 1 month and 2 months to determine the stability of the peroxide delivery systems as a function of stabilizer level in the hydrogen peroxide solution, as well as to determine the effect of impurity level and pH of the solid support on the peroxide stability. The results are presented in Table 6.

The level of stabilizer present in the peroxide delivery systems likewise has an effect on the long-term stability of the peroxide in the peroxide delivery systems. Preferably at least 1 ppm of any individual stabilizer is present in the peroxide delivery system, more preferably at least 10 ppm, better still at least 3000 ppm and most preferably at least 9000 ppm, although any level of stabilizer that is typically used to prevent premature degradation of the peroxide is

TABLE 6

Retention of active oxygen in peroxide delivery systems.

| Silica | Impurity level | pH of silica | $H_2O_2$ loading, weight % | Stabilizer level* | Active oxygen 1 week 50° C., % initial | Active oxygen 1 month 50° C., % initial | Active oxygen 2 months 50° C.; % initial |
|---|---|---|---|---|---|---|---|
| Sipernat ® 500 LS | High | ≈6.0 | 35% | Very High 1 | 55 | — | — |
| Sipernat ® 22 LS | High | ≈6.2 | 35% | Very High 1 | 31 | — | — |
| Aeroperl ® 300 Pharma | Low | 3.5-5.5 | 25% | High 4 | 96 | — | — |
| Syloid ® 244 FP | Medium | 7.0 | 28% | Medium 2 | 78 | — | — |
| CAB-O-SIL ® M-5P | (expected to be low) | 3.6-4.5 | 35% | Medium 2 | 96 | — | — |
| CAB-O-SIL ® M-5F | Low | 3.6-4.5 | 35% | Medium 2 | 100 | — | — |
| CAB-O-SIL ® EH5F | (expected to be low) | 3.6-4.5 | 35% | Medium 2 | 99 | — | — |
| Aerosil ® 300 Pharma | Low | 3.7-4.7 | 35% | Medium 2 | 98 | — | — |
| Aerosil ® 200 Pharma | (expected to be low) | 3.5-5.5 | 35% | Medium 2 | 100 | — | — |
| CAB-O-SIL ® M-5F | Low | 3.6-4.5 | 35% | Very low 3 | 82 | 8 | — |
| CAB-O-SIL ® M-5F | Low | 3.6-4.5 | 35% | High 4 | 100 | 96 | 91 |
| CAB-O-SIL ® M5 | Low | 3.6-4.5 | 35% | High 4 | 100 | 100 | 91 |
| Aerosil ® 200 | (expected to be low) | 3.7-4.5 | 35% | High 4 | 99 | 100 | 71** |
| Aerosil ® 300 | Low | 3.7-4.5 | 35% | High 4 | 100 | 100 | 88** |
| CAB-O-SIL ® EH5F | (expected to be low) | 3.6-4.5 | 49% | Medium 5 | — | — | 97 |
| Aerosil ® 300 Pharma | Low | 3.7-4.7 | 49% | Medium 5 | — | — | 98 |
| Aerosil ® 300 Pharma | Low | 3.7-4.7 | 35% | High 4 | 99 | 97 | 88 |
| CAB-O-SIL ® EH5F | (expected to be low) | 3.6-4.5 | 35% | High 4 | 99 | 96 | 91 |
| Aerosil ® 200 Pharma | (expected to be low) | 3.5-5.5 | 35% | High 4 | 100 | 100 | 91 |
| Aerosil ® 300 | Low | 3.7-4.5 | 35% | Medium 2 | 98 | 95 | 99 |
| CAB-O-SIL ® M5 | Low | 3.6-4.5 | 35% | Medium 2 | 96 | 95 | 100 |
| Aeroperl ® 300 Pharma | Low | 3.5-5.5 | 25% | High 4 | 96 | — | — |
| CAB-O-SIL ® M-5P | (expected to be low) | 3.6-4.5 | 35% | High 4 | 96 | 94 | 80 |

*The peroxide solutions are designated as follows: 1 is Peroxal ® 50% CG-HP; 2 is Peroxal ® 50% CG; 3 is Peroxal ® 50% EG; 4 is Peroxal ® 50% CLG; 5 is Peroxal ® 70% CG.

**75 days (2.5 months)

It is apparent from these results that the hydrogen peroxide in the peroxide delivery systems showed significantly higher stability when loaded on silica which does not contain any, or contains a minimal amount of, Al, Ca, Fe, K, Mg, Ti and Zr, as detailed in Table 5. For optimum stability of the peroxide delivery system, the amount of each of the impurities or contaminants should be below 50 ppm, more preferably below 16 pm, still more preferably below 10 ppm and most preferably less than 5 ppm.

suitable. The exact peroxide stabilizer system is also not particularly limited and any typical peroxide stabilizers or stabilizer systems or mixtures thereof are suitable to use in the peroxide delivery system disclosed herein.

Finally, the pH of the solid support used in the peroxide delivery system also affects the long-term stability of the peroxide in the peroxide delivery system. Preferably, the pH of the solid support should be below 6 and most preferably below 5.5.

Example 3: Surface Moisture on Peroxide Delivery System

This in-house test was established to assess the amount of liquid, if any, present at the surface of the powder loaded with hydrogen peroxide. If free liquid were present at the surface of the powder, it would quickly be transferred to an absorbent material.

A small strip of thin paper (cut from 1 ply AccuWipe brand #29712 by Georgia-Pacific) 10 cm long by 1 cm wide, able to absorb many times its own weight in liquid was added to Aerosil® 200 silica and one strip was added to the peroxide delivery system loaded with 35% hydrogen peroxide (CG grade) in Aerosil® 200 silica. Each strip of paper was re-weighed after being immersed in the powders for 24 hours at 25° C. Table 7 shows the results of this experiment.

TABLE 7

| Silica | Peroxide loading | Strip weight (g) | Strip weight (g) | Weight gain after 24 hours (g) | Weight gain After 24 hours | Appearance |
|---|---|---|---|---|---|---|
| Aerosil® 200 | control | 0.0477 | 0.0479 | 0.0002 | 0.42% | Dry |
| Aerosil® 200 | 35% | 0.0436 | 0.0488 | 0.0052 | 11.9% | Dry |

As expected, due to the equilibrium between the powder and its environment, a minimal gain weight was observed when the paper strip is left in direct contact with the 35% Aerosil® 200 powder. Some residual powder remained on each strip. A quick air blow from a compressed air cylinder was directed at the paper strips to remove as much residual powder as possible before weighing, but it was still difficult to assess how much of the observed weight gain was due to powder sticking to the paper and how much was due to the actual moisture absorption. The paper felt completely dry after removal from the peroxide delivery system. Any moisture absorption is likely due to an equilibrium established between the paper and the peroxide delivery system.

These results show clearly that virtually no moisture is present on the surface of the peroxide delivery system. "Dry to the touch" is thus established to mean that a 1 ply AccuWipe brand #29712 by Georgia-Pacific absorbs less than 15% moisture by weight after being immersed in the peroxide delivery system for 24 hours at 25 degrees C.

Example 4: Peroxide Delivery System for Stain Removal on Fabric

The effect of the dry powder peroxide delivery stem as a direct stain remover was tested as follows:
Two standardized swatches of fabric were tested:
Cotton Soiled with Blood—STC EMPA 111 cut 3"×4"
Bill (blue) Berry Juice on Cotton—STC CFT CS-15 cut 3"×4"
(Both swatches sourced from Testfabrics, Inc. 415 Delaware Ave., West Pittston, Pa. 18643—www.testfabrics.com).

Three different peroxide delivery system powders containing 35% hydrogen peroxide, 17.5% and 8.75%, respectively were directly rubbed dry (no added water) onto the blood and berry juice (FIG. 3b) stained cotton swatches.

The fabric swatches treated with the peroxide delivery system powders were allowed to stand for approximately 10 minutes.

Figure 3A:
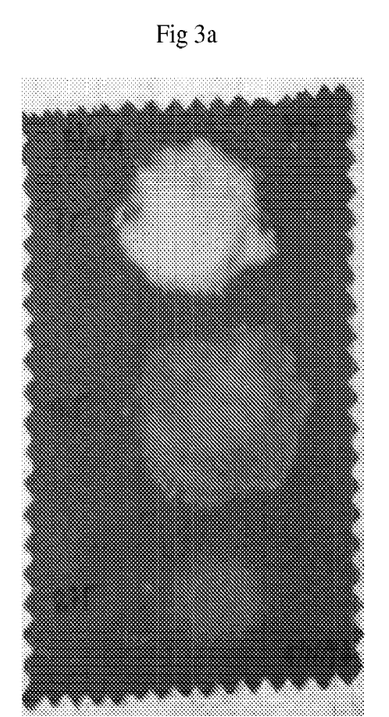
FIGS. 3a and 3b show stain removal efficacy of an embodiment of the invention.
Figure 3B:
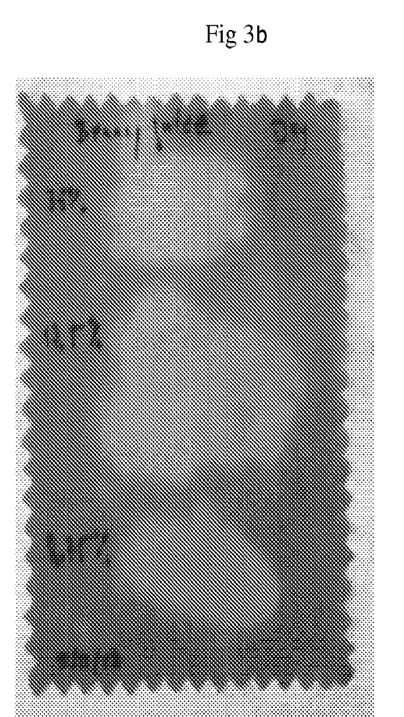

The powder was then rinsed off the swatches with water.
FIG. 3a shows the blood stained fabric swatch after this peroxide treatment, with the 35% hydrogen peroxide at the top, 17.5% in the center and 8.75% near the bottom. FIG. 3b is the berry stained swatch, again with the 35% hydrogen peroxide at the top, 17.5% in the center and 8.75% near the bottom.

Removal of the stain is observed (white spots) in both swatches. The removal of the blood stain appears to be more dependent on the concentration of peroxide in the peroxide delivery system in that a higher concentration of peroxide was needed for effective stain removal than for the berry juice stain.

Other non-limiting examples of applications for the peroxide delivery system disclosed herein are any application where a peroxide would be useful, e.g. as an antiseptic for personal hygiene, for cleaning, or for bleaching laundry or teeth. The peroxide delivery system can be made into preparations of powders, liquids, foams, sprays, gels, ointments, creams, or pastes, and be tabletted in various forms and shapes to be used for a variety of cleaning, stain removal and antiseptic products. Other non-limiting uses are cosmetic applications such as creams and ointments or bleaching systems for hair or skin as well as for use in hair dye compositions requiring an oxidizer; personal care such as deodorants and washing products; oral care such as tooth whitening, toothpastes, powders that can be mixed into mouthwash; cleaning applications, for instance carpet cleaning powder or powders to mix with water to make a peroxide solution; stain removal applications, such as for laundry, either for direct stain removal or formulated with laundry detergent powders; formulated into cleaning pods for laundry or dish detergent; and odor removal from rooms or refrigerators or other enclosed spaces, for instance cars.

Various exemplary aspects of the present invention may be summarized as follows:

A delivery system for at least one peroxide compound comprising an inorganic solid support and at least one peroxide compound. The inorganic solid support is inert to the peroxide compound and also can adsorb a liquid while remaining dry to the touch. The peroxide compound is a liquid peroxide or is in a liquid solution. The liquid peroxide or the liquid solution is combined with the inorganic solid support, which forms the delivery system for the at least one peroxide compound.

The liquid peroxide or the liquid solution may also contain a stabilizer, a mixture of stabilizers or a stabilizer system for the peroxide compound.

The pH of inorganic solid support can be less than 6. The inorganic solid support preferably has less than 50 ppm of any of Al, Ca, Fe, K, Mg, Ti, or Zr. Fumed silica is a preferred material for the inorganic support. The fumed silica may be hydrophilic fumed silica. The peroxide compound in liquid may be a solution of hydrogen peroxide in water. The aqueous solution of hydrogen peroxide also may contain at least one stabilizer for the hydrogen peroxide.

The fumed silica can have less than 50 ppm of any of these individual contaminants: Al, As, Ba, Ca, Cd, Co, Cr, Cu, Fe, K, Mg, Mn, Mo, Na, Ni, P, Pb, Sb, Si, Sn, Sr, Ti, V, W, Zn, or Zr. The fumed silica may contain less than 50 ppm of any of these individual contaminants: Al, Ca, Fe, K, Mg, Ti, or Zr. The fumed silica can have less than 10 ppm of any of these individual contaminants: Al, Ca, Fe, K, Mg, Ti, or Zr.

The peroxide delivery may contain hydrophilic fumed silica and a solution of hydrogen peroxide in water. The solution of hydrogen peroxide in water can further contain a suitable stabilizer for the hydrogen peroxide. The level of peroxide stabilizer in the peroxide delivery system can be 0.001% by weight of the stabilizer for hydrogen peroxide.

The peroxide delivery system has a total delivery system weight and the liquid peroxide or the peroxide compound in liquid solution has a liquid peroxide weight or a peroxide liquid solution weight and the weight of the liquid peroxide or the weight of the peroxide liquid solution makes up at least 70% of the total delivery system weight. The weight of the liquid peroxide or the weight of the peroxide liquid solution can make up at least 50% of the total delivery system weight.

If a solution of hydrogen peroxide in water is used, the hydrogen peroxide can be at least 50% by weight of the solution. If a solution of hydrogen peroxide in water is used, the hydrogen peroxide can be at least 70% by weight of the solution.

The peroxide compound used in the peroxide delivery system may be at least one of hydrogen peroxide, peracetic acid, perborates, percarbonates, organic peroxides, persulfate salts, or peroxyacids.

Suitable peroxide stabilizers for the peroxide in the peroxide delivery system include: stannates, polyols, diols, carboxylates, phosphates, pyrophosphates, ethylenediaminetetraacetic acid (EDTA) and salts thereof, amine-substituted organophosphonic acids and their salts, adipic acid and salts thereof, phosphoric acid and salts thereof, succinic acid and salts thereof, butylated hydroxytoluene (BHT), butylated hydroxyanisole (BHA), phenols, and mixtures thereof.

An exemplary delivery system for at least one peroxide compound is disclosed. The system comprises fumed silica. The fumed silica is inert to the at least one peroxide compound and has a pH less than 6. The fumed silica is capable of adsorbing up to 70% of a liquid by weight of the delivery system while remaining dry to the touch. The fumed silica also contains less than 50 ppm of any individual of these contaminants: Al, Ca, Fe, K, Mg, Ti, and Zr. The at least one peroxide compound may be a liquid peroxide or a liquid solution of peroxide compound. The liquid peroxide or the liquid solution of peroxide is capable of being adsorbed by the fumed silica. The liquid peroxide or the liquid solution of peroxide contains at least 0.001% by weight of a stabilizer for the peroxide. Up to 70% of the liquid peroxide or the liquid solution of peroxide by weight of the delivery system is combined with the fumed silica, which forms the delivery system for the peroxide compound.

An exemplary hydrogen peroxide delivery system is disclosed. The hydrogen peroxide delivery system is comprised of hydrophilic fumed silica and a solution of hydrogen peroxide in water. The hydrophilic fumed silica is inert to hydrogen peroxide and has a pH less than 6. The silica is also capable of adsorbing up to 70% of water by weight of the delivery system while remaining dry to the touch, and further, contains less than 50 ppm of any of these contaminants: Al, Ca, Fe, K, Mg, Ti, and Zr. The solution of hydrogen peroxide in water is capable of being adsorbed by the hydrophilic fumed silica and contains at least 0.001% by weight of a stabilizer for the hydrogen peroxide.

The peroxide in the peroxide delivery system can have an initial active oxygen content and at least 60% of the initial active oxygen content may be retained after storage for 1 week at 50° C. The peroxide in the peroxide delivery system can have an initial active oxygen content and at least 80% of the initial active oxygen content may be retained after storage for 1 week at 50° C. The peroxide in the peroxide delivery system can have an initial active oxygen content and at least 90% of the initial active oxygen content may be retained after storage for 1 week at 50° C.

Also disclosed is a method of removing stains from stained fabric. The method comprises the steps of: a) providing the peroxide delivery system according to any of the embodiments described herein; b) applying the peroxide delivery system to the stained fabric; c) allowing the peroxide delivery system to stand on the stained fabric for a period of time (i.e., contacting the peroxide delivery system with the stained fabric for a period of time); and d) rinsing the peroxide delivery system from the stained fabric (using water, for example).

Also disclosed is an oral care composition comprising the peroxide delivery system or a toothpaste or tooth cleaning composition comprising the peroxide delivery system.

The peroxide delivery system may also be formulated into a cleaning composition. Exemplary such cleaning systems are those that are used to clean, for instance, laundry, kitchens, or floors, or for other general cleaning purposes.

The peroxide delivery system may be also formulated into cosmetic compositions to be used for bleaching of skin or hair or for general antiseptic purposes.

Hair bleaching compositions can comprise the peroxide delivery system. Hair dye compositions also may comprise the peroxide delivery system.

Antiseptic compositions intended for a variety of disinfecting purposes can comprise the peroxide delivery system disclosed herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A delivery system for at least one peroxide compound comprising:
   a) a hydrophilic inorganic solid support selected from the group consisting of precipitated silica, fumed silica and mixtures thereof, wherein the hydrophilic inorganic solid support is inert to the at least one peroxide compound and is capable of adsorbing a liquid while remaining dry to the touch; and
   b) the at least one peroxide compound, wherein the at least one peroxide compound is a liquid peroxide or is in a liquid solution and is capable of being adsorbed by the hydrophilic inorganic solid support;
   whereby the at least one peroxide compound is adsorbed by the hydrophilic inorganic solid support while the hydrophilic inorganic solid support remains dry to the touch, thereby forming a dry to the touch delivery system for the at least one peroxide compound; wherein the delivery system comprises at least one stabilizer for the at least one peroxide compound; and
   wherein the at least one peroxide compound has an initial active oxygen content and wherein the at least one peroxide compound retains at least 80% of the initial active oxygen content after storage for 1 week at 50° C.

2. The delivery system for the at least one peroxide compound according to claim 1, wherein the hydrophilic inorganic solid support has a pH less than 6.

3. The delivery system for the at least one peroxide compound according to claim 1 wherein the hydrophilic inorganic solid support comprises less than 50 ppm of any individual contaminant selected from the group consisting of Al, Ca, Fe, K, Mg, Ti, and Zr.

4. The delivery system for the at least one peroxide compound according to claim 1, wherein the at least one peroxide compound comprises a solution of hydrogen peroxide in water.

5. The delivery system for the at least one peroxide compound according to claim 4 wherein the solution of hydrogen peroxide in water comprises at least 70% hydrogen peroxide.

6. The delivery system for the at least one peroxide compound according to claim 5 wherein the solution of hydrogen peroxide in water comprises at least 50% hydrogen peroxide.

7. The delivery system for the at least one peroxide compound according to claim 1, wherein the fumed silica has a pH less than 6.

8. The delivery system for the at least one peroxide compound according to claim 1 wherein the fumed silica comprises less than 50 ppm of any individual contaminant selected from the group consisting of Al, As, Ba, Ca, Cd, Co, Cr, Cu, Fe, K, Mg, Mn, Mo, Na, Ni, P, Pb, Sb, Si, Sn, Sr, Ti, V, W, Zn, and Zr.

9. The delivery system for the at least one peroxide compound according to claim 1 wherein the fumed silica comprises less than 50 ppm of any individual contaminant selected from the group consisting of Al, Ca, Fe, K, Mg, Ti, and Zr.

10. The delivery system for the at least one peroxide compound according to claim 1, wherein the fumed silica comprises less than 10 ppm of any individual contaminant selected from the group consisting of Al, Ca, Fe, K, Mg, Ti, and Zr.

11. The delivery system for the at least one peroxide compound according to claim 1 wherein the at least one peroxide compound comprises a solution of hydrogen peroxide in water.

12. The delivery system for the at least one peroxide compound according to claim 11, wherein the solution of hydrogen peroxide in water comprises at least 0.001% by weight of the stabilizer for the hydrogen peroxide.

13. The delivery system for the at least one peroxide compound according to claim 11 wherein the solution of hydrogen peroxide in water comprises at least 70% hydrogen peroxide.

14. The delivery system for the at least one peroxide compound according to claim 1 wherein the liquid peroxide weight or the liquid solution weight comprises at least 70% of the total delivery system weight.

15. The delivery system for the at least one peroxide compound according to claim 1 wherein the liquid peroxide weight or the liquid solution weight comprises at least 50% of the total delivery system weight.

16. The delivery system for the at least one peroxide compound according to claim 1, wherein the at least one peroxide compound is selected from the group consisting of hydrogen peroxide, peracetic acid, perborates, percarbonates, organic peroxides, persulfate salts, peroxyacids, and mixtures thereof.

17. The delivery system for the at least one peroxide compound according to claim 1, wherein the at least one stabilizer is selected from the group consisting of stannates, polyols, diols, carboxylates, phosphates, pyrophosphates, ethylenediaminetetraacetic acid (EDTA) and salts thereof, amine-substituted organophosphonic acids and their salts, adipic acid and salts thereof, phosphoric acid and salts thereof, succinic acid and salts thereof, butylated hydroxytoluene (BHT), butylated hydroxyanisole (BHA), phenols, and mixtures thereof.

18. The delivery system for the at least one peroxide compound according to claim 1, wherein the at least one peroxide compound has an initial active oxygen content and wherein the at least one peroxide compound retains at least 90% of the initial active oxygen content after storage for 1 week at 50° C.

19. A delivery system for at least one peroxide compound comprising:
a) hydrophilic fumed silica, wherein the fumed silica is inert to the at least one peroxide compound, is capable of adsorbing up to 70% of a liquid by weight of the delivery system while remaining dry to the touch, has a pH less than 6, and contains less than 50 ppm of any individual contaminant selected from the group consisting of Al, Ca, Fe, K, Mg, Ti, and Zr; and
b) the at least one peroxide compound wherein the at least one peroxide compound is a liquid peroxide or is a solution of the at least one peroxide compound in liquid and is capable of being adsorbed by the fumed silica;
whereby up to 70% of the liquid peroxide or the solution of the at least one peroxide compound in liquid by weight of the delivery system is adsorbed by the hydrophilic fumed silica while the hydrophilic fumed silica remains dry to the touch, thereby forming a dry to the touch delivery system for the at least one peroxide compound; wherein the delivery system comprises at least 0.0001% of at least one stabilizer for the at least one peroxide compound; and
wherein the at least one peroxide compound has an initial active oxygen content and wherein the at least one peroxide compound retains at least 80% of the initial active oxygen content after storage for 1 week at 50° C.

20. A delivery system for hydrogen peroxide comprising:
a) hydrophilic fumed silica, wherein the hydrophilic fumed silica is inert to hydrogen peroxide, is capable of adsorbing up to 70% of liquid by weight of the delivery system while remaining dry to the touch, has a pH less than 6, and contains less than 50 ppm of any individual contaminant selected from the group consisting of Al, Ca, Fe, K, Mg, Ti, and Zr; and
b) a solution of hydrogen peroxide in water, wherein the solution of hydrogen peroxide in water comprises at least 0.0001% of at least one stabilizer for the hydrogen peroxide and is capable of being adsorbed by the hydrophilic fumed silica;
whereby up to 70% of the solution of hydrogen peroxide in water by weight of the delivery system is adsorbed by the hydrophilic fumed silica while the hydrophilic fumed silica remains dry to the touch, thereby forming a dry to the touch delivery system for hydrogen peroxide; and
wherein the solution of hydrogen peroxide in water has an initial active oxygen content and wherein the solution of hydrogen peroxide in water retains at least 80% of the initial active oxygen content after storage for 1 week at 50° C.

21. A dry to the touch delivery system for at least one peroxide compound comprising: (a) a hydrophilic inorganic solid support selected from the group consisting of precipitated silica, fumed silica and mixtures thereof; and (b) the at least one peroxide compound, wherein the at least one peroxide compound is a liquid peroxide or is in a liquid solution and is capable of being adsorbed by the hydrophilic inorganic solid support; produced by adsorbing the liquid peroxide in or the liquid solution to the hydrophilic inorganic solid support while the hydrophilic inorganic solid support remains dry to the touch thereby forming the dry to the touch delivery system for the at least one peroxide compound; wherein the delivery system comprises at least one stabilizer for the at least one peroxide compound; and wherein the at least one peroxide compound has an initial active oxygen content and wherein the at least one peroxide compound retains at least 80% of the initial active oxygen content after storage for 1 week at 50° C.

22. The dry to the touch delivery system for the at least one peroxide compound according to claim 21, wherein the hydrophilic inorganic solid support has a pH less than 6.

23. The dry to the touch delivery system for the at least one peroxide compound according to claim 21 wherein the hydrophilic inorganic solid support comprises less than 50 ppm of any individual contaminant selected from the group consisting of Al, Ca, Fe, K, Mg, Ti, and Zr.

24. The dry to the touch delivery system for the at least one peroxide compound according to claim 21, wherein the at least one peroxide compound comprises a solution of hydrogen peroxide in water.

25. The dry to the touch delivery system for the at least one peroxide compound according to claim 24 wherein the solution of hydrogen peroxide in water comprises at least 70% hydrogen peroxide.

26. The dry to the touch delivery system for the at least one peroxide compound according to claim 24 wherein the solution of hydrogen peroxide in water comprises at least 50% hydrogen peroxide.

27. The dry to the touch delivery system for the at least one peroxide compound according to claim 21, wherein the hydrophilic fumed silica has a pH less than 6.

28. The dry to the touch delivery system for the at least one peroxide compound according to claim 21 wherein the hydrophilic fumed silica comprises less than 50 ppm of any individual contaminant selected from the group consisting of Al, As, Ba, Ca, Cd, Co, Cr, Cu, Fe, K, Mg, Mn, Mo, Na, Ni, P, Pb, Sb, Si, Sn, Sr, Ti, V, W, Zn, and Zr.

29. The dry to the touch delivery system for the at least one peroxide compound according to claim 21 wherein the hydrophilic fumed silica comprises less than 50 ppm of any individual contaminant selected from the group consisting of Al, Ca, Fe, K, Mg, Ti, and Zr.

30. The dry to the touch delivery system for the at least one peroxide compound according to claim 29, wherein the hydrophilic fumed silica comprises less than 10 ppm of any individual contaminant selected from the group consisting of Al, Ca, Fe, K, Mg, Ti, and Zr.

31. The dry to the touch delivery system for the at least one peroxide compound according to claim 29 wherein the at least one peroxide compound comprises a solution of hydrogen peroxide in water.

32. The dry to the touch delivery system for the at least one peroxide compound according to claim 31, wherein the solution of hydrogen peroxide in water comprises at least 0.001% by weight of the at least one stabilizer for the hydrogen peroxide.

33. The dry to the touch delivery system for the at least one peroxide compound according to claim 31 wherein the solution of hydrogen peroxide in water comprises at least 70% hydrogen peroxide.

34. The dry to the touch delivery system for the at least one peroxide compound according to claim 21 wherein the liquid peroxide weight or the liquid solution weight comprises at least 70% of the total delivery system weight.

35. The dry to the touch delivery system for the at least one peroxide compound according to claim 21 wherein the liquid peroxide weight or the liquid solution weight comprises at least 50% of the total delivery system weight.

* * * * *